(12) United States Patent
Tindall et al.

(10) Patent No.: US 6,351,982 B1
(45) Date of Patent: Mar. 5, 2002

(54) HOUSING FOR A FLAMMABLE GAS DETECTOR

(75) Inventors: Ian Francis Tindall, Bournemouth; Russell Christopher Foot, Poole; Martin Charles Legg, Dorset, all of (GB)

(73) Assignee: Zellweger Analytics Limited, Dorset (GB)

( * ) Notice: Subject to any disclaimer, the term of this patent is extended or adjusted under 35 U.S.C. 154(b) by 0 days.

(21) Appl. No.: 09/485,756

(22) PCT Filed: Aug. 18, 1998

(86) PCT No.: PCT/GB98/02469

§ 371 Date: Feb. 15, 2000

§ 102(e) Date: Feb. 15, 2000

(87) PCT Pub. No.: WO99/09409

PCT Pub. Date: Feb. 25, 1999

(30) Foreign Application Priority Data

Aug. 18, 1997 (GB) .............................................. 9717462

(51) Int. Cl.⁷ ........................ G01N 33/00; G01N 33/22; G01D 11/24
(52) U.S. Cl. ........................ 73/23.31; 73/431; 264/35; 340/693.5
(58) Field of Search ................................ 73/23.31, 431, 73/31.02, 31.03, 31.05; 340/632, 693, 693.5, 693.6; 422/94, 95, 96, 97; 29/595; 264/35

(56) References Cited

U.S. PATENT DOCUMENTS

| | | | |
|---|---|---|---|
| 4,263,588 A | | 4/1981 | Gautier ........................ 340/632 |
| 4,317,868 A | * | 3/1982 | Spiegelberg .................. 429/82 |
| 4,352,099 A | * | 9/1982 | Christen et al. ............. 340/633 |
| 5,215,835 A | * | 6/1993 | Jones .......................... 427/101 |
| 5,331,310 A | | 7/1994 | Stetter et al. ................ 340/632 |
| 5,481,904 A | * | 1/1996 | Fleck, Sr. et al. .......... 73/61.51 |
| 5,495,747 A | * | 3/1996 | Herman et al. ............. 73/23.21 |
| 5,709,187 A | * | 1/1998 | Jaeger et al. ............ 123/198 D |

FOREIGN PATENT DOCUMENTS

| | | | | |
|---|---|---|---|---|
| EP | 432962 | | 6/1991 | |
| GB | 2 339 474 | * | 1/2000 | ................ 73/23.31 |
| JP | 58-146845 | * | 9/1983 | |
| JP | 5-99871 | * | 4/1993 | ................ 73/23.31 |
| WO | 84/04967 | * | 12/1984 | |

OTHER PUBLICATIONS

Shigeo "Preparation of Flame Arrestor for Gas Sensor" Patent Abstracts of Japan (60–80749) May, 1985.*

* cited by examiner

*Primary Examiner*—Thomas P. Noland
(74) *Attorney, Agent, or Firm*—Andrus, Sceales, Starke & Sawall, LLP

(57) ABSTRACT

A housing for flammable gas detector comprises a housing body and a flame arrestor element (14 and 15). The housing body has an aperture (27) in which the flame arrestor element is located through which the interior of the housing body communicates with the outside. The housing body surrounding the aperture is molded from plastic material. The portions of the housing body that form the aperture (27) are molded around the flame arrestor element with the flame arrestor element in situ. A flammable gas detector of the type which employs a heated sensing element to oxidize any flammable gas present may be located in the housing body. Any flame front present in the housing body due to oxidation of any flammable gas is prevented from progressing to the surrounding environment by the flame arrestor element.

10 Claims, 4 Drawing Sheets

HOUSING FOR A FLAMMABLE GAS DETECTOR

BACKGROUND OF THE INVENTION

This invention relates to a housing for a flammable gas detector.

One type of flammable gas detector employs a heated sensing element to oxidize any flammable gas present. Oxidation of flammable gases at the sensing element causes a change in electronic properties of the sensor which is detected to indicate the presence of a flammable gas. For example, a catalytic bead sensing element may comprise a coil of wire embedded in a porous bead containing a catalyst. The bead is heated electrically by passing current through the wire. If flammable gas is present at the bead, it oxidizes exothermally in the presence of the catalyst, causing the temperature of the bead, and hence the wire coil, to increase. The change in resistance resulting from the change in temperature is detected to indicate the presence of a flammable gas. Frequently two bead elements are used in a Wheatstone bridge arrangement with one element acting as the sensor and the other being of similar construction but rendered inert and acting as a control. Higher output, and hence greater sensitivity, can be obtained by using multiple beads connected in series or through the use of electronic amplification of the output signal.

Although, for operation of the detector, the gas within the detector housing must communicate with the surrounding ambient gases, for reasons of safety, the gas undergoing oxidation within the housing must be prevented from igniting any flammable a as outside the housing. For this purpose, known detectors include in the wall of the housing a flame arrestor in the form of a sinter element, through which the interior of the housing communicates with the outside. The flame arrestor should provide as small a resistance to diffusion as is consistent with its primary requirements of strength and quenching the flame front.

The housing for the sensor must be flameproof and capable of withstanding internal explosion without allowing a flame front to propagate outside the housing. Any joint or gaps in the housing must be small enough to attenuate the flame front such that it is incapable of igniting the gas outside the housing.

Known housings are cast from metal. All potential flame paths require 100% inspection in order for the housing to meet the relevant safety standards. Not only must the flame arrestor element be itself designed to meet the required safety standards but it must be secured to the housing in such a way as to prevent a flame path being provided at the flame arrestor element/housing interface. In order to form a satisfactory flame arresting arrangement, the housing and sinter element must be in intimate contact along the entire length of the sinter element/housing interface. The periphery of the sinter element, and the internal surface of the housing over the region of contact with the sinter element, must be precisely formed. In practice to meet the tight tolerances required for satisfactory performance, the cast metal housing has to be precision machined.

In manufacturing the known flammable gas detectors, the sinter element is fixed to the housing in a separate operation. The sinter element may be glued to the housing, or the housing may be peened over the sinter element, or the sinter element may be retained in the housing by peening the housing over the edges of the sinter element, and the sinter element subsequently glued in position.

The precision machining, quality assurance and fixing operations required to ensure that the known housings meets safety standards, makes them time-consuming and expensive to manufacture.

SUMMARY OF THE INVENTION

According to the present invention there is provided a housing for a flammable gas detector comprising a housing body with an aperture through which the interior of the housing body communicates with the outside, a gas permeable flame arrestor element located in the aperture, at least a portion of the housing body surrounding the aperture being molded from plastic materials, the portions of the housing body that form the aperture being molded around the flame arrestor element with the flame arrestor element in situ whereby the flame arrestor element is fixed to the housing body. Molding the body of the plastic housing around the flame arrestor element with the flame arrestor element in situ eliminates the operation of fixing the flame arrestor element into the housing. Moulding the plastic material directly onto the periphery of the flame arrestor element elimnates the flame path at the interface between the arrestor element and the housing. The requirements for machining the housing, and fixing the sinter element to the housing in a separate operation are eliminated reducing the overall number of manufacturing operations with subsequent savings in both manufacturing time and cost.

A suitable plastic material is used for the housing body. It should exhibit which impact strength mechanical rigidity, UV stability and flame retardant properties over an extensive temperature range. Suitable plastics might be thermoplastic, for example mineral-filled PPS (polyphenylsulphide), PBT (polybutylterepthalate), or LCP (liquid crsystal polymer such as poly(benzoate-napthoate)). Alternatively, thermosetting plastics such as DMC (dough-molding compound-polyester) might be used.

The porous nature of sinter elements allows any hot plastic which comes into contact with the sinter element to be wicked into the sinter element, reducing the gas permeability of the sinter element and, therefore, its effectiveness. When a sinter element which has a support ring around its periphery is used, the housing can be designed so that the hot plastic comes into contact only with the support ring and never into direct contact with the porous sinter element.

If the housing is to be molded around a sinter element which does not have a support ring, wicking may be reduced, or eliminated, by using a sinter element which has a greater density around its periphery where the housing and the sinter element will be joined, than in the middle. By making the periphery denser, the pore size is reduced and the molten plastic material cannot penetrate the sinter material so easily where it comes into contact with the housing.

BRIEF DESCRIPTION OF THE SEVERAL VIEWS OF THE DRAWING

Preferred embodiments of the invention will now be described in more detail with reference to the drawings in which.

DETAILED DESCRIPTION OF THE INVENTION

Figure 1:
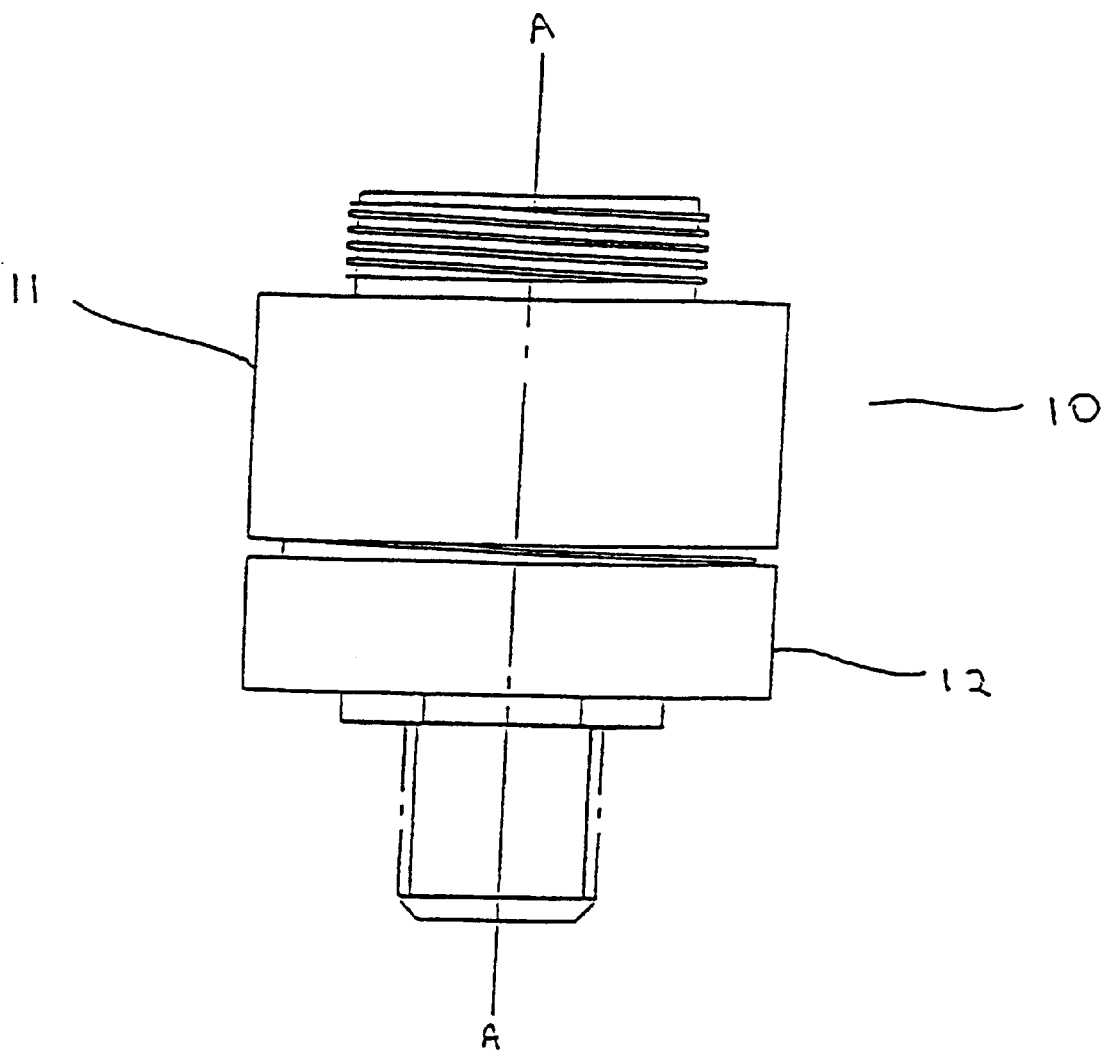
FIG. 1 is a side elevation of the housing.
Figure 2:
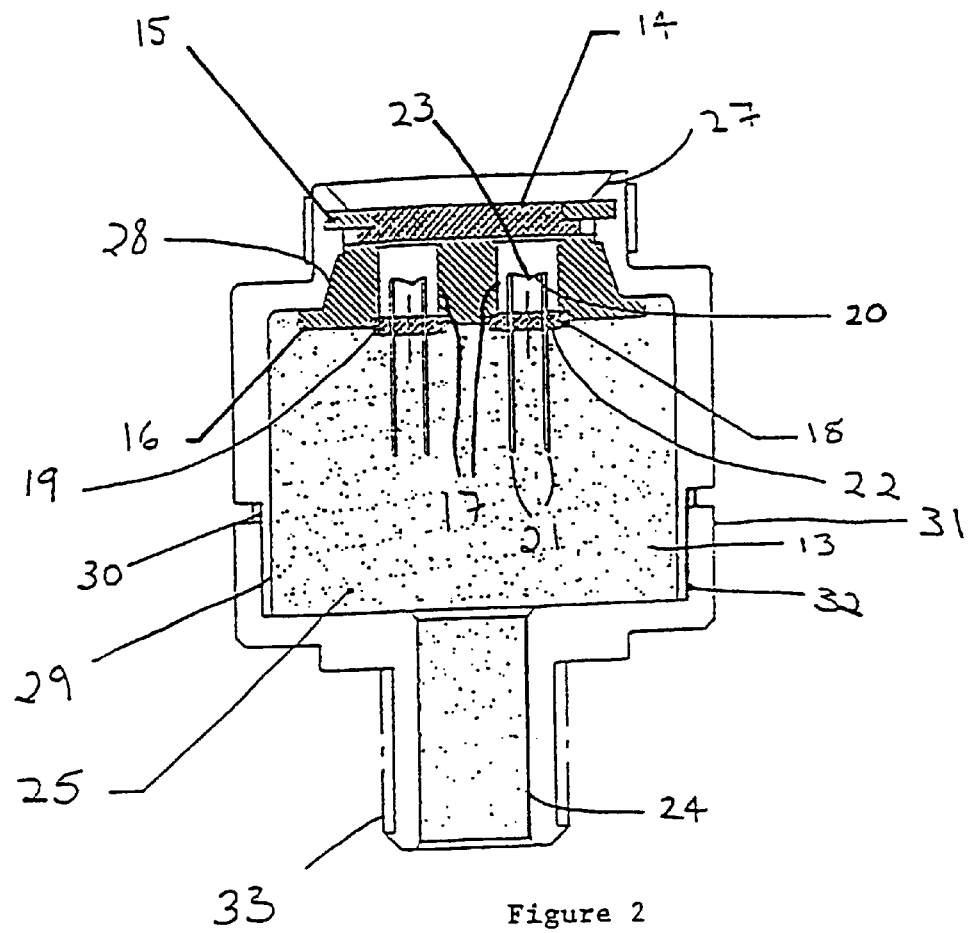
FIG. 2 is a section through the housing of FIG. 1 along the line A—A showing a sinter element with a support ring.

FIGS. 1 and 2 show a housing 10 for a flammable gas detector. The housing consists of two parts 11 and 12 which screw together to form an enclosed chamber 13. A porous sinter element 14 of the type provided with a support ring 15 is mounted at one end of the housing and provides the means by which the interior of the housing communicates with the outside.

The housing 10 accommodates the sensing elements of the flammable gas detector. A sensor retainer 16 in the form of a flanged circular disc with two axially-extending holes 17 locates a sensing element 18 and a reference element or control 19 within the housing. The elements 18 and 19 are of similar construction. Although the embodiment shown in the drawings has a single sensing element and a single reference element, other arrangements are possible. For example the sensor retainer may locate multiple beads connected in series for the sensing element and the reference element.

The sensing element 18 consists a heater wire 20 connected between two lead-in conductors 21 which are mounted in a supporting block 22. A bead 23 of catalyst material distributed over a porous substrate is formed around the heater wire.

The reference element is identical to the sensing element except that the bead is inert, either because the catalyst material is omitted or because the catalyst has been deliberately poisoned.

The lead-in conductors of the elements are connected to the outside by leads (not shown) which pass through a sleeve portion 24 of reduced diameter at the opposite end of the housing to the sinter element 14. The housing of the assembled detector is filled with an encapsulant 25 such as epoxy resin.

The sensing element and the reference element are connected into opposite arms of a Wheatstone Bridge circuit (not shown). An electric current is passed through the heater wires 20 of the elements 18 and 19 and heats the beads 23. In the absence of flammable gases, the resistances of the two elements 18 and 19 are the same and the arms of the Wheatstone bridge are balanced resulting in no voltage drop across the arms.

If there is a flammable gas present in the ambient atmosphere around the housing 10, some will diffuse through the sinter element 14 into the holes 17 in which the sensing and reference elements 18 and 19 are located. The presence of the heated catalyst on the bead of the sensing element 18 causes any flammable gases around it to oxidize in an exothermic reaction. This reaction heats the bead of the sensing element 18 and causes the temperature of its heating wire to increase, which, in turn, causes the resistance of the sensing wire to increase. The increase in resistance of the sensing element 18 compared with the resistance of the reference element 19 causes the Wheatstone Bridge to become unbalanced and a voltage drop across the bridge is detected to indicate the presence of the flammable gas.

The construction of the housing will now be described in more detail. The first part 11 of the housing 10 is made by molding plastic material around the support ring 15, which supports the sinter element it. One part of a die, the female die, has a raised circular core. The sinter element is centered over the raised circular core such that the entire periphery of the support ring 15 overhangs the raised core. The male die has a smaller cross-sectional area, fitting inside the female die and locating onto and around the sinter element such that the sinter element 14 is entirely enclosed between the male die and the core of the female die keeping the plastic material from coming into contact with the sinter element. Hot plastic material is injected into the die mold, and allowed to set.

Figure 3:
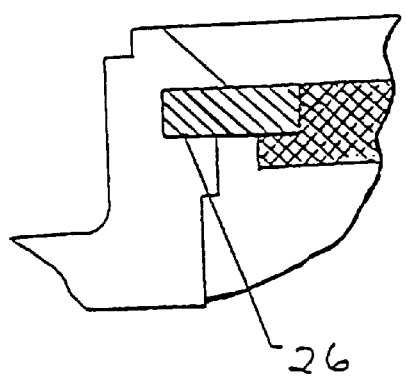
FIG. 3 is an enlarged section of the sinter element/housing junction of FIG. 2.

The plastic material which now incorporates the sinter element is turned out of the mold to form the first part 10 of the housing as shown in FIGS. 2 and 3. The molded interface 26 between the plastic first part 11 of the housing 10 and the support ring 15 avoids the creation 14 of any flame path between the housing and the support ring whilst retaining the properties of the sinter element, namely its gas permeability and its ability to quench a flame front. The first part of the rousing manufactured in this way has one end formed with an aperture 27 which is closed by the sinter element 14, the other end 29 being open and having an external screw thread 30.

The sensor retainer 16 fits inside the first part 11 of the housing, locating against the interior face of the sinter element 14 and a shoulder 28 formed on the inside of the housing. The sensor retainer holds the sensing and reference elements 18 and 19 in the required positions on the inside of the sinter element 14.

The second part 12 of the housing 10 is also molded of plastic material. One end 31 of the part 12 has an internal screw thread 32 which matches the external screw thread 30 at the end 29 of the first part 11 and allows the two parts to be screwed together to form the enclosed chamber 13.

The other end 33 of the second part of the housing is formed with an integral sleeve 24 of reduced diameter to allow electrical connection of the sensing and reference elements to the electrical circuitry of the Wheatstone Bridge (not shown). With the sensor retainer 16 holding the elements 18 and 19 in position, in the first part of the housing, the two parts 11 and 12 are screwed together. The end of the chamber 13 between the retainer 16 and the sleeve 24 is then filled with an epoxy resin encapsulant 25, sealing the interior of the housing, apart from the holes 17 which accommodate the elements 18 and 19, from the environment.

The housing is molded from a plastic material which will provide satisfactory performance at the operation temperatures which the detector is likely to experience. Suitable thermoplastics include, but are not limited to, mineral filled polyphenylsulphide, polybutylterephtalate, and liquid crystal polymer such as poly(benzoate-napthoate). Alternatively thermosetting plastics such as dough molding compound-polyester may be used.

Figure 4:
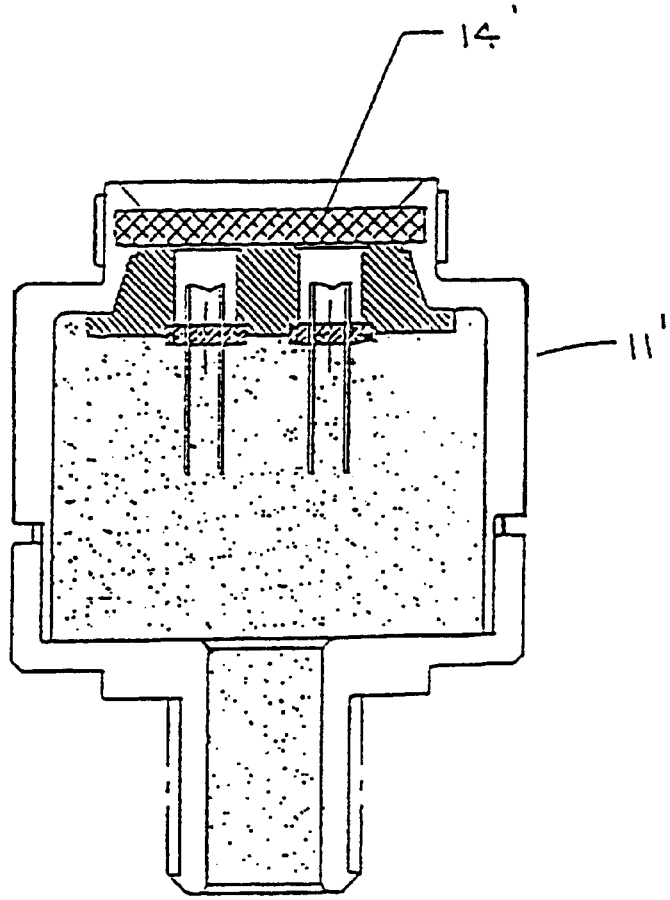
FIG. 4 is a section of the housing of FIG. 1 along the line A—A showing a sinter element without a support ring.
Figure 5:
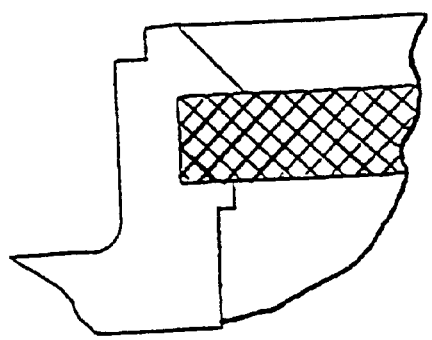
FIG. 5 is an enlarged section of the sinter element/housing junction of FIG. 4.

FIGS. 4 and 5 show an alternative embodiment of the invention, in which the sinter element has no support ring and the first part 11' of the housing is molded directly onto the sinter element 14' itself, so that the sinter element is in intimate contact with the first part of the plastic housing. In order to prevent hot plastic of the housing from wicking into the sinter element 14' during the injection molding process, the sinter element is manufactured with an increase density around its periphery which results in the center portion of the sinter element remaining permeable to gases, and the peripheral portions of the sinter element being less susceptible to wicking of the hot plastic.

Figure 6:
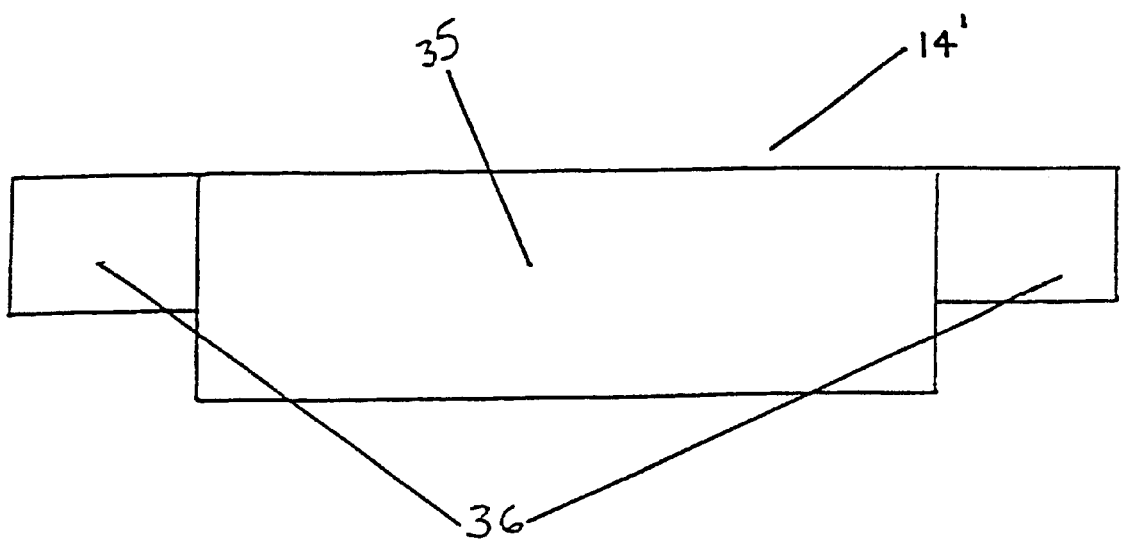
FIG. 6 shows a sinter element which has increased density around its periphery.

FIG. 6 shows a sinter element 14' which has been manufactured to provide a gas permeable central portion 35 and denser peripheral portions 36. Sinter elements of this type may be manufactured in a variety of ways. Flame arrestors, in the form of sinter elements, may be produced by pouring powdered metal of a known grain size into a mold which forms one half of a die set. The second half of the die set is lowered and pressure is applied to the powder allowing some of the particles to bond together in a brittle biscuit-like form known as a green-state sinter. This green sinter is then fired in a furnace, the firing normally being performed in a reducing atmosphere to ensure that the powder remains in the metallic state. In the final sintered structure the metal particles are fused together giving the structure great strength while at the same time providing many routes for gas to pass through the sinter element albeit over a distance far greater than the thickness of the sinter element. A flame front present in the interior of a detector housing may also commence along these paths. However, the combination of the high thermal conductivity of the metal particles and the length of the path through which the flame front must travel to reach the side of the sinter element in contact with the surrounding environment ensures that any flame front is quenched before it reaches the surrounding environment. The sinter element presents very little resistance to the passage of gases.

One method for producing a sinter element with increased sinter density around its periphery is to produce a normal, flat green state sinter element which is then placed in a second die such that an increased pressure is applied only to the periphery of the sinter element only. The periphery therefore is compressed further and the powder particles become more densely packed. The sinter is then fired in the normal way, using a combination of reducing furnaces. By applying sufficient pressure to the periphery during the manufacturing process it can be made so dense in the finished product that wicking is reduced or even eliminated. The resultant sinter element has a gas permeable center section 35 and a denser periphery 36 which is less susceptible to wicking and which may even be totally impervious to gas.

In another method the initial die set can be constructed so that the powder is poured evenly into the mold and the second half of the die set has a recessed center portion. When pressure is applied to the second half of the die, the periphery of the sinter has greater pressure applied than the center portion. When fired as above, the sinter element produced has a gas permeable center section 35 and denser peripheral sections 36 which are less susceptible to wicking.

In a third method the sinter can be made of two powders, a coarse powder in the center and a fine powder toward the edge. Uniform pressure is applied A form the sinter. By the nature of the smaller grain size of fine powder a more dense and impermeable sinter is made at the outside. By manufacturing a sinter element with a denser periphery, the need for a support ring is avoided, and sinter elements may be manufactured more cheaply.

In alternative embodiments, the sinter element may be constructed by placing a greater thickness or powdered metal particles at the periphery so that in the finished article the thickness of the element is uniform with the periphery having a greater density than the center.

What is claimed is:

1. A housing for a flammable gas detector comprising: a housing body with an aperture through which the interior of the housing body communicates with the outside; and a gas permeable flame arrestor element located in the aperture for receiving flammable gases into the housing, said flame arrestor element comprising a sinter element in which the density of the sinter element is greater around the periphery of the sinter element than in the center of the sinter element, said flame arrestor element arresting the propagation of a flame front through the aperture to the outside in the event of an explosion within the housing, at least a portion of the housing body surrounding the aperture comprising a plastic material, said plastic material housing body portion being molded around the flame arrestor element to form said plastic material housing body portion and said flame arrestor element into an integral component in which the flame arrestor element is bonded and sealed about its periphery to said plastic material housing body portion to preclude a path for a flame front originating in the housing and said plastic material housing body portion is formed around the flame arrestor element to mechanically constrain the flame arrestor element from being dislodged from said aperture by an explosion within said housing.

2. A housing for a flammable gas detector according to claim 1 wherein the plastic material housing body portion is injection molded around the flame arrestor element.

3. A housing for a flammable gas detector according to claim 1, wherein the sinter element is provided with increased density of sinter around its periphery by a second pressing of unfired, green-state sinter.

4. A housing for a flammable gas detector according to claim 1, wherein the sinter element is provided with an increased density of sinter around its periphery by a single molding operation using a stepped or graduated mold.

5. A housing for a flammable gas detector according to claim 1, wherein the sinter element is provided with an increased density of sinter around its periphery by the presence of a fine grain powder around the periphery and a coarser grain powder in the center.

6. A housing for a flammable gas detector according to claim 1 wherein the material of the housing is thermoplastic and is mineral filled polyphenylsulphide, polybutyltereptha-late or poly(benzoate-napthaoate).

7. A housing for a flammable gas detector according to claim 1, wherein the plastic material of the housing is thermosetting and is a dough molding compound-polyester.

8. A housing for a flammable gas detector according to claim 1, wherein the flame arrestor element includes a support ring, the support ring being disposed around the sinter element and the plastic material of the housing body being molded onto the support ring.

9. A method for forming a component for a housing of a flammable gas detector, said method comprising the steps of:

providing a mold for the housing component;

placing a gas permeable, sinter flame arrestor element in the mold; and supplying plastic material to the mold and around the sinter flame arrestor element which is in situ in the mold to form the housing component in the mold and to bond and seal the component so formed to the periphery of the flame arrestor element so that the housing component and flame arrestor element are formed into an integral component devoid of a path for a flame front originating in the housing and in which the flame arrestor element is mechanically constrained from being dislodged from the housing component by an explosion within the housing.

10. A method according to claim 9 including forming the sinter element from powdered metal, the periphery of the sinter element being compressed to form a material of greater density than at the center.

* * * * *